United States Patent [19]

Booth et al.

[11] 4,227,027

[45] Oct. 7, 1980

[54] RECYCLABLE BORON TRIFLUORIDE CATALYST AND METHOD OF USING SAME

[75] Inventors: Robert E. Booth; Francis E. Evans, both of Hamburg; Richard E. Eibeck, Orchard Park; Martin A. Robinson, Amherst, all of N.Y.

[73] Assignee: Allied Chemical Corporation, Morris Township, Morris County, N.J.

[21] Appl. No.: 96,955

[22] Filed: Nov. 23, 1979

Related U.S. Application Data

[63] Continuation-in-part of Ser. No. 951,911, Oct. 16, 1978.

[51] Int. Cl.$^3$ ............................ C07C 3/56; C07C 3/18
[52] U.S. Cl. ...................... 585/465; 585/525
[58] Field of Search ................ 585/465, 525, 644, 726

[56] References Cited

U.S. PATENT DOCUMENTS

| | | | |
|---|---|---|---|
| 2,425,839 | 8/1947 | Schulze et al. | 585/435 |
| 3,382,291 | 5/1968 | Brennan | 585/521 |
| 3,780,128 | 12/1973 | Shubkin | 585/525 |
| 3,957,664 | 5/1974 | Heilman et al. | 252/49.6 |
| 4,032,591 | 6/1977 | Cupples et al. | 585/643 |
| 4,045,507 | 8/1977 | Cupples et al. | 585/511 |
| 4,045,508 | 8/1977 | Cupples et al. | 585/511 |
| 4,172,855 | 10/1979 | Shubkin | 585/16 |

*Primary Examiner*—Curtis R. Davis
*Attorney, Agent, or Firm*—Alan M. Doernberg; Jay P. Friedenson

[57] ABSTRACT

When saturated with boron trifluoride, certain polyhydric alcohols form adducts which catalyze hydrocarbon alkyl transfer reactions for which boron trifluoride is catalytic. The adduct is recovered from the reaction mixture and recycled, greatly reducing boron and fluoride values in the product and in any effluent. Examples include propylation of toluene in the presence of a recycled adduct of boron trifluoride with mannitol or sorbitol, and the oligomerization of decene by a recycled adduct of boron trifluoride with mannitol or butanediol. Some of the catalysts become viscous on cooling and are thus more easily separated from the reaction products which remain in a separate liquid phase.

10 Claims, No Drawings

RECYCLABLE BORON TRIFLUORIDE CATALYST AND METHOD OF USING SAME

DESCRIPTION

This is a continuation-in-part of U.S. Pat. No. application Ser. No. 951,911, filed Oct. 16, 1978.

BACKGROUND OF THE INVENTION

Boron trifluoride has found wide use as a catalyst for various reactions and has been proposed as a catalyst for additional reactions. Such reactions include hydrocarbon transfers (alkylations, cracking, isomerizations, polymerizations) and reactions involving functional groups (dehydration of alcohols, cyanation of olefins, conversions of aniline to diphenylamine, conversion of methylol to 4-methoxy-2-methyl-1-butene, reaction of ammonia and acrolein to form pyridine and reaction of sodium acetate and acetylene to form vinyl acetate). A drawback of the use of boron trifluoride is that it decomposes during reaction, preventing reuse and contributing boron and fluoride to either the product or an effluent stream, necessitating extra purification or recovery.

While attempts have been made to fix boron trifluoride to a polymer or inorganic support, these attempts have not produced a reusable boron trifluoride catalyst system practical for the wide variety of catalytic uses. For many particular reactions, a cocatalyst is provided with boron trifluoride to cause or enhance catalytic activity. Such cocatalysts have not, however, been used to retain the boron and fluoride values.

Specifically, the alkylation of aromatics such as the propylation of benzene is described in U.S. Pat. No. 2,425,839 to Schulze et al. (Aug. 19, 1947) using monohydric alcohol-boron trifluoride addition compounds. The oligomerization of alpha olefins such as the oligomerization of alpha-decene with adducts of monohydric alcohols and boron trifluoride is described in the following U.S. Pat Nos.: 3,780,128 Shubkin et al. (Dec. 18, 1973); 4,032,591 Cupples et al. (June 28, 1977); 4,045,507 Cupples et al. (Aug. 30, 1977); 4,045,508 Cupples et al. (Aug. 30, 1977); 3,957,664 Heilman et al. (May 18, 1977); 3,382,291 Brennan (May 7, 1968).

Additional $BF_3$ gas feed and/or saturation of the hydrocarbon with $BF_3$ are at least preferred by all three Cupples patents, the Brennan patent and the Shubkin patent.

Polyols such as ethylene glycol, propylene glycol and glycerol are discussed, but not exemplified, in several of these references as co-catalysts in place of monohydric alcohols.

BRIEF DESCRIPTION OF THE INVENTION

It has been discovered that certain polyhydric alcohols form stable complexes or adducts with boron trifluoride which can catalyze reactions for which boron trifluoride is a catalyst and which can be separated from the reaction mixture with minimum loss of activity or boron and fluoride values.

Accordingly, the present invention includes an improvement in a method of reacting at least one unsaturated hydrocarbon in an alkyl transfer reaction of the type catalyzed by boron trifluoride. In the improvement, the reaction is conducted in the presence of a catalytic amount of a butanediol saturated with boron trifluoride to form an adduct and the adduct is recovered from the product of the reaction and is recycled.

Allowed application Ser. No. 951,911 relates to the use of similar adducts, but not specifically butanediols.

The present invention also includes stable, recyclable catalyst adducts formed by the saturation with boron trifluoride of a polyhydric alcohol selected from the group consisting of butanediols, tetritols, pentitols, hexitols, heptitols, pentaerythritol, crystalline polysaccharides and non-adjacent diols of 5–10 carbons.

DETAILED DESCRIPTION OF THE INVENTION

The stable catalyst adducts of the present invention are formed by saturation of polyhydric alcohols with $BF_3$. The product is referred to herein as an "adduct" without limitation as to its actual structure which, because of the observed ratio of one mole of $BF_3$ to two moles of hydroxyl in some cases, may be a chelate of the formula

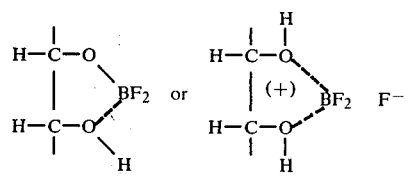

The present invention is not, however, limited to alcohols with hydroxyls on adjacent carbons.

The polyhydric alcohols of the present invention include linear members of the formula $CH_2OH$—$(CHOH)_n$—$CH_2OH$ where n is 1 to 5, branched polyhydric alcohols having 3–6 hydroxyls such as pentaerythritol, polyvinyl alcohol and certain polysaccharides. The linear polyhydric alcohols include the tetritols erythritol and threitol (D or L or racemic); the pentitols ribitol, xylitol and arabitol (D or L or racemic); the hexitols dulcitol, sorbitol, mannitol (D or L of racemic), iditol (D or L or racemic), talitol (D or L or racemic) and allitol; and the heptitols which include perseitol and sedoheptitol. Preferred are the hexitols and especially preferred are mannitol and sorbitol.

The polyhydric alcohols of the present invention also include diols with non-adjacent hydroxyls of 4–10 carbons such as 2,4-pentane diol. Preferred in this group are diols of 5–10 carbons of the formula $R_1$—$CHOH$—$CH_2$—$CHOH$—$R_2$ where $R_1$ and $R_2$ are each alkyl of 1–6 carbons and together have 2–7 carbons.

The polyhydric alcohols of the present invention also include 1,3-butanediol, 1,4-butanediol and 2,3-butanediol. 1,2-butanediol, 1,2-propanediol (propylene glycol) and ethylene glycol are suitable, but not preferred.

Certain monohydric alcohols such as butanol and decanol also form adducts with boron trifluoride that are active for the reactions contemplated, and in some cases are more active than the present catalysts. It is also possible, though difficult, to recover and recycle the adducts of monohydric alcohols. It appears, however, that such adducts of monohydric alcohols leave higher levels of boron and fluoride in the product than the present catalysts. Furthermore, although recycling of monohydric alcohol-$BF_3$ adduct was contemplated by certain prior art disclosures, the significance of low boron and fluoride levels in the product was clearly not appreciated as indicated, for example, by the addition of gaseous $BF_3$ to the reaction mixture during each cycle.

Branched polyhydric alcohols having 3–6 hydroxyls are also suitable, and preferred in this group is pentaerythritol $C(CH_2OH)_4$.

Some, but not all sugars, both pentoses and hexoses, are suitable. Crystalline polysaccharides are also suitable, such as crystalline cellulose and some starches; while non-crystalline polysaccharides such as cellulose fiber and sucrose are generally unsuitable.

The first criterion for polyhydric alcohols suitable in the present invention is that they absorb $BF_3$ gas in substantial proportions. It appears that a minimum of about 0.3 moles $BF_3$ absorbed per mole of hydroxyls is required. Many but not all polyhydric alcohols tested which absorb such substantial quantities of $BF_3$ are active for one pass of alkylation or similar reaction. The second criterion for the polyhydric alcohol-$BF_3$ adduct is that it be separable from the product mixture of alkylation or similar reaction, either by distillation, decanting or some other technique, preferably by decanting based upon immiscibility or insolubility or solidification of the catalyst adduct on cooling. The third criterion is that the adduct be catalytically active for at least one additional pass of alkylation or similar reaction and preferably for at least four additional passes. Most preferred are adducts formed from polyhydric alcohols such as mannitol, sorbitol, butanediols, crystalline cellulose and pentaerythritol which give substantially constant activity on succeeding passes of alkylation.

The quantity of $BF_3$ absorbed varies, even among isomers such as mannitol (which absorbed about 3 moles $BF_3$) and sorbitol (which absorbed about 2 moles). Optical isomers such as D-mannitol and L-mannitol and mixtures thereof such as racemic mannitol would be expected to behave similarly. It is postulated that the stereochemical differences between, for example, sorbitol and mannitol cause one pair of adjacent hydroxls to be good $BF_3$ acceptors in mannitol but poor $BF_3$ acceptors in sorbitol. The behavior of glycerin and xylitol in absorbing more $BF_3$ moles than the number of hydroxyl pairs suggests that the odd hydroxyl is also somewhat active. The resistance of the inositol used suggests a conformational arrangement which prevents $BF_3$ absorption, but does not necessarily indicate that other stereoisomers are inactive. The catechol adduct only lasted one run, at least for the cymene reaction, because it failed to be easily separable from the alkylation product mixture in which it dissolved. Catechol and other polyhydric aromatics such as resorcinol are not, therefore, excluded provided that a suitable separation technique is used.

Of the polysaccharides tested, crystalline cellulose, starch and sucrose all gave absorption of at least about 0.3 moles $BF_3$ per mole and all three were active on the first pass. Sucrose and starch would be regarded, however, as unsuitable because of failure to retain activity after separation. Cellulose fiber failed to absorb $BF_3$ and could thus be rejected on the first criterion.

The reactions for which the present catalysts may be used are not limited to alkylations. Other hydrocarbon transfer reactions involving at least one unsaturated reactant, such as isomerizations, cracking and polymerizations for which boron trifluoride is catalytically active, may be conducted in the presence of the catalyst adducts. In addition, reactions involving functional groups such as cyanation of olefins, formation of pyridine and formation of vinyl acetate, may be practised with the catalyst adducts.

Reaction conditions may be similar to those used for the same reaction with boron trifluoride alone as catalyst. Because many of the catalyst adducts solidify at moderate temperatures, it is frequently desirable to maintain the reaction mixture at slightly elevated temperatures such as 40°–120° C. with agitation. Ceasing agitation, cooling or both frequently causes separation of catalyst adduct from the reaction mixture, enabling recovery and recycling by phase separation. With some reactions, it may be more convenient to distill the product from the reaction mixture, leaving the catalyst adduct for reaction with fresh reactant.

The ratio in each pass or in a continuous system at one time of catalyst adduct to reagent (monomer in the case of oligomerizations, the limiting reagent in the case of alkylations or other reactions between reagents) is not critical, but may be in the range of about 0.0001 to 10:1 with about 0.001 to 1:1 being preferred and about 0.005 to 0.1:1 being more preferred.

EXAMPLE 1

Propylation of Toluene with Mannitol-$BF_3$ Adduct $BF_3$ gas was passed into a stirred slurry of mannitol (50 g, 0.276 mole) and toluene (207 g) (dried of excess moisture by azeotropic distillation) at room temperature for seven hours. The adduct had separated as a gummy mass that could be agitated only at elevated temperatures. $BF_3$ addition was continued at 60°–70° for 16 hours, and 50°–60° for seven hours (viscosity had decreased somewhat). The mannitol absorbed 57.7 g $BF_3$, 0.851 mole, which is 3.1 moles $BF_3$ per mole of mannitol, and 0.51 mole $BF_3$ per hydroxyl group.

The toluene was decanted from the adduct (an immobile gum at room temperature) and fresh toluene (about 200 g) was stirred with adduct at about 60° with a $N_2$ purge to strip unreacted $BF_3$. When gas chromatography analysis of the toluene phase showed no $BF_3$, the toluene was again replaced, and propylene passed into the toluene-adduct mixture agitated at 62° for 3 hours. Gas chromatography analysis of the liquid phase showed it to contain 20.5% p-cymene. (The chromatogram has peaks that are probably attributable to o-cymene, and dipropyl-toluenes, but proof and quantitative determinations were not available for these.) The product mixture (200 g), decanted from the catalyst, was extracted twice with 200 mL water; analysis of the combined extracts showed the toluene-cymene product had 248 ppm boron and 590 ppm fluoride. The catalyst was washed by stirring at 60° with fresh toluene to remove cymenes.

Fresh toluene was added to the catalyst and stirred 2 hours at 60°; it now showed 0.8% p-cymene extracted from the catalyst. Propylene was passed in with agitation at 60°–80° for three hours. Analysis showed the toluene phase to be 44.5% p-cymene, or a gain of 43.7%. Water extraction and analysis showed that the toluene phase contained 87 ppm boron and 221 ppm fluoride.

In like manner the catalyst performed through two additional cycles. The conditions and results of all four cycles are displayed in Table 1.

Table 1

| Cycle | 1 | 2 | 3 | 4 |
|---|---|---|---|---|
| Propylation (hrs) | 5 | 3 | 3 | 3 |
| Temperature (°C.) | 62 | 60–80 | 65–86 | 60–63 |
| Initial p-cymene (vol. %) | 0 | 0.8 | 0.8 | 2.0 |
| Final p-cymene (vol. %) | 20.5 | 44.5 | 44 | 40 |

Table 1-continued

| Cycle | 1 | 2 | 3 | 4 |
|---|---|---|---|---|
| Gain in p-cymene | 20.5 | 43.7 | 43.2 | 38 |
| Boron content of product (ppm) | 248 | 87 | — | 20 |
| Fluoride content of product (ppm) | 59 | 221 | 149 | 99 |

Other batches of mannitol-boron trifluoride adduct wereused over ten and five cycles.

EXAMPLE 2

Propylation of Toluene With Sorbitol-BF₃ Adduct.

In a procedure like that described in Example 1, BF₃ was added to sorbitol (50 g., 0.276 mole) at temperatures up to 85° (whatever temperature was required to preserve mobility through the grummy stages) over a 19 hour period. 40.7 g. BF₃ (0.600 mole) was absorbed, (equivalent to 2.17 moles per mole sorbitol or 0.36 per hydroxyl).

Propylation of toluene by this catalyst was conducted as detailed in Example 1, but, as shown below, the run time was shortened. In the first cycles, the p-cymene content had leveled off, but the toluene content was about 20%, and dipropyl toluenes showed prominently, indicating that cymene was being propylated more than toluene.

Consequently, the third, fourth and fifth runs were shortened to two, one and one hour. The conditions and results are displayed in Table 2.

Table 2

| Cycle | 1 | 2 | 3 | 4 | 5 |
|---|---|---|---|---|---|
| Propylation (hours) | 3 | 3 | 2 | 1 | 1 |
| Temperature (°C.) | 77°-94° | 91°-98° | 70°-86° | 80°-83° | 75°-81° |
| p-Cymene-initial % | 0.16 | 0.03 | 0.1 | 0.5 | 0.01 |
| p-Cymene-final % | 34 | 40 | 46.5 | 30.5 | 30 |
| p-Cymene-increase % | 33.8 | 40 | 46.5 | 30 | 30 |
| Boron - ppm | 268 | 99 | 214 | 7 | 187 |
| Fluoride - ppm | 511 | 244 | 471 | 28 | 472 |

EXAMPLE 3

Propylation of Toluene With Glycerin-BF₃ Adduct

Following the procedure of Example 1, BF₃ was added to glycerin. Though a liquid, the adduct formed a high-viscosity gum after about seven hours of adding BF₃ and required warming at 40°-50° for continued agitation. The BF₃ saturated product contained 1.93 moles BF₃ per mole of glycerin (0.64 per hydroxyl), and propylated toluene as shown in Table 3.

Table 3

| Cycle | 1 | 2 | 3 | 4 | 5 |
|---|---|---|---|---|---|
| Propylation (hours) | 3 | 3 | 3 | 3 | 3 |
| Temperature (°C.) | 54°-67° | 55°-67° | 56°-67° | 54°-72° | 50°-68° |
| p-Cymene-initial % | <0.1 | 0.3 | 0.6 | 0.4 | 1.0 |
| p-Cymene-final % | 20.5 | 21.3 | 25.5 | 30.0 | 25.5 |
| p-Cymene-increase % | 20.5 | 21.0 | 24.9 | 29.6 | 24.5 |

EXAMPLE 4

Propylation of Toluene with Xylitol-BF₃ Adduct

Following the procedure of Example 1, BF₃ (26.0 g, 0.383 mole) was added to xylitol (25.3 g, 0.166 mole) at 40°-50°. The xylitol absorbed 2.30 moles BF₃ per mole, or 0.46 per hydroxyl, and propylated toluene as shown in Table 4.

Table 4

| Cycle | 1 | 2 | 3 |
|---|---|---|---|
| Time - hours | 3 | 3 | 3 |
| Temperature | 52°-61° | 51°-57° | 52°-64° |
| p-Cymene - initial % | <0.01 | 0.25 | 1.1 |
| p-Cymene - final % | 22 | 15 | 8 |
| p-Cymene - increase % | 22 | 14.8 | 6.9 |

Examples 7, 11, 15 and 18 and Comparative Examples 5, 6, 8-10, 12-14, 16, 17 and 19

Other Adducts

Following the procedure of Example 1, BF₃ addition of the other polyhydric alcohols shown in Table 5 was attempted, followed by propylation of toluene (except in Comparative Examples 10 and 16 where no BF₃ had been absorbed). Propylation temperatures were adjusted to control viscosity of the adduct and ranged from 40°-50° C. with less viscous adducts to 90°-105° with mor viscous adducts. The results of these Examples and Comparative Examples, and the previous four Examples, are summarized in Table 5.

Table 5

| | | BF₃ Addition | | Propylation | |
|---|---|---|---|---|---|
| Ex. | Polyhydric Alcohol | BF₃ Mole/Mole | BF₃ Mole/OH | %p-Cymene | No. of Cycles |
| 1 | Mannitol | 3.1 2.9 | 0.50 | 35-44% | 5 |
| 2 | Sorbitol | 2.2 2.1 | 0.36 | 35-40%[a] | 5 |
| 3 | Glycerin | 1.9 | 0.64 | 20-30% | 5 |
| 4 | Xylitol | 2.3 | 0.46 | 22,15,7[b] | 3 |
| C 5 | Starch | 2.4 | 0.79 | 13% | 1 |
| C 6 | Cellulose (fiber) | 0.2 | 0.07 | 1% | 1 |
| 7 | Cellulose (xtal) | 2.5 | 0.82 | 15-35% | 5 |
| C 8 | Sucrose | 2.7 | 0.34 | 3% | 1 |
| C 9 | Methyl Glucoside | 2.0 | 0.50 | 3% | 1 |
| C 10 | Inositol | 0 | 0 | — | — |
| 11 | Pentaerythritol | 1.8 | 0.45 | 13-18 | 5 |
| C 12 | Dipentaerythritol | 3.0 | 0.50 | 1% | 1 |
| C 13 | Catechol | 1.0 | 0.50 | 12%[d] | 1 |
| C 14 | Ascorbic Acid | [c] | | 3% | 1 |
| 15 | Polyvinyl Alcohol | | | 6% | 2 |
| C 16 | Oxalic Acid | 0 | 0 | — | — |
| C 17 | Triethanolamine | [c] | — | 7% | 1 |
| 18 | 2,4-Pentanediol | 2.1 | 1.07 | 45-56% | 3 |
| C 19 | Poly(hydroxy-methylene)[e] | 0 | 0 | — | — |

[a]With Sorbitol-BF₃, the % p-cymene was about constant in 3-hr. runs, but toluene was nearly exhausted and poly-propyltoluenes very much in evidence. One-hour runs produced 30% p-cymene.
[b]The percentages decreased as shown over three cycles, indicating the adduct was decomposing and was not completely recyclable.
[c]Ratio not determned but apparently in excess of 1.
[d]The catechol-BF₃ adduct was not recyclable here - it totally dissolved in the toluene-cymene mixture (though not originally soluble in toluene alone).
[e]A polymer of the formula H—(CHOH)$_n$—H formed by the homopolymerization of vinylidene carbonate and hydrolysis of the product.

It should be appreciated that cellulose fiber (C6), inositol (C10), oxalic acid (C16) and poly(hydroxymethylene) (C19) are unsuitable polyhydric alcohols by virtue of the inability to meet the first criterion by absorbing BF₆. Starch (C5), sucrose (C8), methyl glucoside (C9), dipentaerythritol (C12), ascorbic acid (C14) and triethanolamine (C17) fail either the second criterion of catalytic activity or the third criterion of recyclability. Catechol (C13) also fails the third criterion, but might be suitable in other BF₃ catalyzed reactions, especially those not involving aromatics. Polyvinyl alcohol (15) is regarded as suitable, but not preferred, because of its limited recyclability. Xylitol (4) is also less preferred because of apparent degradation on recycling. Of the additional adducts tested, only those formed from pentaerythritol (11) and crystalline cellulose (7) retained activity on recycling, but at a level lower than 2,4-pentanediol and the preferred hexitols: mannitol and sorbitol.

EXAMPLE 20

Polymerization of Diisobutylene With Mannitol-BF$_3$ Adduct

Mannitol.BF$_3$ catalyst was prepared by the addition of BF$_3$ (35.8 g, 0.528 mole) to mannitol (31.2 g, 0.171 mole) in toluene over a 24 hour period at 50°–60°. The adduct contained 3.08 moles BF$_3$ per mole mannitol, or 0.51 mole per hydroxyl. All toluene was decanted from the catalyst. Dropwise addition of diisobutylene was begun at room temperature (about 7 mL/min.). An exothermic reaction heated the mixture to 62° in 15 minutes. After holding at 62° for 20 additional minutes, external heating was applied. Diisobutylene (213 mL, 152 grams) was added in 35 minutes, and the reaction mixture was held at 53°–62° for an additional 4½ hours. The decanted liquid phase had a Brookfield viscosity of 11.0 centipoise (diisobutylene—1.0 cps). Distillation of the liquid phase delivered about 30 g. at 180°–190° (this must be the dimer: tetraisobutylene; diisobutylene boils at 101°–102° C.). The clear, yellow, oily residue has a Brookfield viscosity of 10.0 cps.

As a control for the above experiment, diisobutylene was polymerized by the diethyl ether complex of BF$_3$. To 162 g diisobutylene stirring at room temperature in a flask, BF$_3$-diethyl ether complex (27.7 g) was added dropwise over a 10 minute period. An exotherm peaked at 61° in 7 minutes, then external heating was applied to hold the mixture at 60°–70° for 6½ hours. At room temperature the mixture separated into two layers: the lower layer (about 24 g) proved to be mainly ether; the upper layer (about 165 g) was washed five times with water to decompose and remove spent BF$_3$, dried over CaCl$_2$ and distilled. A few drops collected at 30°–40° (ether), then nothing until 25 g was collected at 180°–190°. The clear, yellow, oily residue has a Brookfield viscosity of 21.0 cps.

It will be appreciated that the control produced lower yields of tetraisobutylene (comparable in physical properties) with an etherate complex that merely fixes the BF$_3$ before reaction in a convenient form for handling, and does not fix the BF$_3$ for recovery and recycling.

EXAMPLE 21

Polymerization of 1-Decene With Mannitol-BF$_3$ Adduct

Mannitol.BF$_3$ catalyst was prepared by the addition of BF$_3$ (53.7 grams, 0.792 mole) to mannitol (50 grams, 0.274 mole) in toluene over a 23 hour period at 60°–70° C. The adduct contained 2.89 moles BF$_3$ per mole of mannitol, or 0.48 mole per hydroxyl. All toluene was decanted from the catalyst and the catalyst was washed with 1-decene to remove the last traces of toluene.

1-Decene (200 mole, 148.2 gram) was agitated with the mannitol.BF$_3$ adduct for 12 hours at 50°–60° C. A chromatogram of a sample of the liquor showed oligomers and great depletion of the decene. The liquor was decanted, washed with concentrated HCl, water, aqueous Na$_2$CO$_3$, four more times with water, dried and distilled (124.2 grams). Fractionation developed three samples (1-Decene boils 172° C.):

| Fr. 1 | b. 144°–160° | 12.7 grams | 10.2% |
|---|---|---|---|
| Fr. 2 | b. 160°–210° | 7.7 grams | 6.2% |
| Fr. 3 | Residue | 103.8 grams | 83.6% |

A chromatogram showed approximately 0.1% low-boilers in Fraction 3, the remainder being oligomers of 1-decene, so a yield of about 84% oligomers is assumed.

This batch of mannitol.BF$_3$ was cycled for three more oligomerizations of 1-decene in about the same manner. Results of all four cycles are tabulated below:

| Cycle | Temp | Time | Oligomer Yield |
|---|---|---|---|
| I | 50°–60° | 12 hr. | 84% |
| II | 55°–70° | 4 hr. | 92% |
| III | 50°–70° | 7 hr. | 94% |
| IV | 50°–55° | 8 hr. | 95% |

EXAMPLE 22

Polymerization of 1-Decene with 1,4-Butanediol-BF$_3$ Adduct 1,4-Butanediol.BF$_3$ catalyst was prepared by addition of BF$_3$ (137.4 g, 2.03 mol) to 1,4-butanediol (90.1 g, 1.00 mol) over 6 h starting and finishing at room temperature. The exotherm was controlled at 63° C. at 90 min by adjustment of the rate of BF$_3$ fed. Decene was dropped on the agitated catalyst as quickly as possible commensurate with controlling the exotherm. Agitation was continued for 4 h at 50°–60° C. Then agitation was stopped and two discernable layers formed without, however, the sharp increase in viscosity of the catalyst layer observed in Example 21. The upper layer was removed and analyzed by gas chromatography for product distribution. The lower layer was weighed (to determine gain of the catalyst layer by absorption of hydrocarbon) and then reused with fresh decene for a second run. The procedure was repeated for a third run as well. The results are tabulated in Table VI:

TABLE VI

| Cycle: | I | II | III |
|---|---|---|---|
| % BF$_3$ on Decene | 39.8% | 40.2% | 40.5% |
| Exotherm: Temp/time | 73°/38 min. | 75°/42 min. | 94°/30 min. |
| Product Lost to Cat. | 9.6% | 4.8% | 0.5% |
| Product Distribution | | | |
| C$_{10}$ | 15.6% | 15.6% | 12.2% |
| C$_{12}$(1) | 2.2 | 1.3 | 0.7 |
| C$_{20}$ | 49 | 46 | 65 |
| C$_{30}$ | 21 | 25 | 14 |
| C$_{40}$ | 12 | 12 | 8 |

(1)The decene contained about 0.5% dodecene; it is not known if these C$_{12}$'s are being formed or concentrated by the present reaction.

EXAMPLE 23

Polymerization of 1-Decene with 1,2-Butanediol.BF$_3$ Adduct 1,2-Butanediol.BF$_3$ catalyst was prepared by addition of BF$_3$ (80.8 g, 1.18 mol) to 1,2-butanediol (90.2 g, 1.00 mol) which had previously been cooled to 0° C. An earlier attempt to prepare the catalyst starting at room temperature caused an uncontrolled exotherm.

1-Decene was dropped onto this catalyst in 25 minutes, controlling an exotherm at 41° by an ice-bath and control of drop-rate. The mixture was cautiously warmed to 60° and the heat source removed. A few minutes later, despite application of ice, an unknown temperature was reached. The mixture was separated into a small catalyst layer (77.1 g—lost 93.3 g) and a large product layer (258.0 g—gained 88.3 g). The layer was washed several times with water which should have removed $BF_3$ and butanediol, and still weighed 211.5 g. A chromatogram of this showed:

$C_{10}$—9.5%
$C_{12}$—10.7%
$C_{20}$—78.8%
$C_{30}$—0.7%
$C_{40}$—0.2%

EXAMPLE 24

Polymerization of 1-Decene with 2,3-Butanediol-$BF_3$ Adduct 2,3-Butanediol.$BF_3$ catalyst was prepared by addition of $BF_3$ (126.5 g, 1.87 mol) to 2,3-butanediol (88.3 g, 0.98 mol) in 27 hours at room temperature. An exotherm was controlled at 48° at 75 minutes. Despite the odd molar ratio 1.90, the diol had taken only 0.7% $BF_3$ the last 8 hours of addition, signaling saturation. Three cycles of decene oligomerization were run substantially as described in Example 22. The results are shown in Table VII:

TABLE VII

| Cycle: | I | II | III |
|---|---|---|---|
| % $BF_3$ | 40.3% | 40.3% | 39.5% |
| Exotherm: Temp/time | 59°/72 min. | 60°/70 min. | 59°/75 min. |
| Product Lost to Cat. | 6.7% | 2.4% | 0 |
| Product Distribution | | | |
| $C_{10}$ | 15.3% | 13.5% | 12.4% |
| $C_{12}$ | 1.8 | — | 0.8 |
| $C_{20}$ | 35.6 | 52.3 | 60.3 |
| $C_{30}$ | 24.2 | 25.9 | 18.0 |
| $C_{40}$ | 12.5 | 8.3 | 8.2 |
| $C_{50}$ | 10.5 | — | — |

EXAMPLE 25

Polymerization of 1-Decene with 1,3-Butanediol-$BF_3$ Adduct 1,3-butanediol-$BF_3$ catalyst was prepared by addition of $BF_3$ (224.6 g, 3.31 mol) to 1,3-butanediol (145.3 g, 1.61 mol) over 23 h. The first six hours of addition was conducted between −5° C. and 25° C. by controlling a strong exotherm with ice. The remainder was at 40°–60° C. except for a second exotherm that reached 105° C. Following the procedure of Example 22, three six and one-half hour cycles of decene polymerization were conducted with product samples taken at 1, 4 and 6½ h. The results of representative samples are displayed in Table VIII.

TABLE VIII

| Cycle: | I (4 h) | II (4 h) | III (4 h) |
|---|---|---|---|
| Exotherm: Temp/time | 52°/30 min | 50°/30 min | 43°/20 min |
| Product Lost to Cat. | 10.4% | 1.7% | not available |
| Product Distribution | | | |
| $C_{10}$ | 7% | 10% | 10% |
| $C_{12}$ | 5% | 2% | 1% |
| $C_{20}$ | 21% | 21% | 54% |
| $C_{30}$ | 32% | 12% | 12% |
| $C_{40}$ | 9% | 10% | 11% |
| $C_{50}$ | 25% | 18% | 9% |

EXAMPLES 26–28

Polymerization of 1-Decene with Mannitol-$BF_3$ Adduct

Several catalysts were prepared as in Example 21 and were used to polymerize 1-decene by the procedures of Example 22 (with the exceptions noted below). The results are displayed in Table IX.

TABLE IX

| Example-Cycle | 26-I | 26-II | 26-III | 26-IV | 27-I |
|---|---|---|---|---|---|
| % $BF_3$ | 43% | 43% | 40% | 36% | 37% |
| Time (hours) | 12 | 4 | 7 | 10 | 5½ |
| Temperature | 50–60 | 50–60 | 50–60 | 50–60 | 50–60 |
| Product Dist. | | | | | |
| $C_{10}$ | 10% | 9% | 8% | 9% | 17% |
| $C_{12}$ | 11 | 2 | 1 | 1 | 0 |
| $C_{20}$ | 64 | 76 | 74 | 68 | 77 |
| $C_{30}$ | 12 | 10 | 12 | 20 | 5 |
| $C_{40}$ | 2 | 2 | 5 | 3 | 1 |
| $C_{50}$ | 0 | 0 | 0 | 0 | 0 |

| Example-Cycle | 28-I | 29-I | 30-I | 30-II |
|---|---|---|---|---|
| % $BF_3$ | 40% | 40% | 40% | 40% |
| Time (Hours) | 4½ | 6 | 24 | 25 |
| Temperature | 100 | 100 | 100 | 50–60 |
| Product Dist. | | | | |
| $C_{10}$ | 11% | 14% | 13% | 17% |
| $C_{12}$ | 0 | 0 | 2 | 0 |
| $C_{20}$ | 71 | 69 | 59 | 74 |
| $C_{30}$ | 18 | 13 | 18 | 9 |
| $C_{40}$ | 4 | 4 | 10 | 0 |
| $C_{50}$ | 0 | 0 | 0 | 0 |

Because reactions with catalysts formed from mannitol are less severely exothermic than those formed from butanediol, the exotherm peak did not exceed the 50°–60° C. or 100° C. initial reaction temperature. Reaction temperature was maintained by external heating. Because of the easier separation of catalyst layer from product layer, no measurement was made of product lost to catalyst.

COMPARATIVE EXAMPLES 31–33

Catalysts were prepared from $BF_3$ and, separately, butanol, decanol and propylene glycol. The amounts absorbed were:

| Example | Alcohol | g (mol) | $BF_3$ g (mol) |
|---|---|---|---|
| C31 | Butanol | 74.1 (1.00) | 72.7 (1.07) |
| C32 | Decanol | 158.3 (1.00) | 69.7 (1.03) |
| C33 | Propylene Glycol | 134.7 (1.77) | 218.2 (3.22) |

Decene polymerizations were conducted as in Example 22 with the results displayed in Table X. The % $BF_3$ in the product and catalyst layer were assayed by gas chromatography and amounts lost or gained based upon amounts charged in each cycle.

TABLE X

| Example-Cycle | 31-I | 31-II | 31-III | 31-IV | 31-V |
|---|---|---|---|---|---|
| % $BF_3$ | 43% | 43% | 43% | 43% | 43% |
| Temperature Peak | 79° C. | 82° C. | 95° C. | 71° C. | 61° C. |
| Product Lost to Cat. | 6.3% | 3.9% | 2.1% | 0.7% | 1.0% |
| Product Dist. | | | | | |
| $C_{10}$ | 5% | 14% | 13% | 10% | 10% |
| $C_{12}$ | 3% | 7% | 5% | 8% | 5% |

TABLE X-continued

| | | | | | |
|---|---|---|---|---|---|
| $C_{20}$ | 34% | 41% | 45% | 46% | 53% |
| $C_{30}$ | 41% | 30% | 32% | 30% | 26% |
| $C_{40}$ | 7% | 6% | 5& | 6% | 5% |
| $C_{50}$ | — | 2% | 0.5% | 0.5% | 0.5% |
| % $BF_3$ Found in product | | 0.7% | 0.3% | 0.6% | 0.4% |
| % $BF_3$ lost in cat | | 1.7% | 0.7% | 0.9% | 0.6% |

| Example-Cycle | 32-I | 32-II* | 33-I (1 h) | 33-I (4 h) |
|---|---|---|---|---|
| % $BF_3$ | 40% | 40% | 39.3 | — |
| Temperature Peak | 89° C. | 48° C.** | 50° C. | — |
| Product Lost to Cat. | 45% | 34% | 5.0% | — |
| Product Dist. | | | | |
| $C_{10}$ | 17 | 14 | 8 | 7 |
| $C_{12}$ | *** | *** | 0.8 | 1 |
| $C_{20}$ | 38 | 27 | 65 | 55 |
| $C_{30}$ | 24 | 24 | 8 | 6 |
| $C_{40}$ | 12 | 12 | 16 | 30 |
| $C_{50}$ | 9 | 23 | 1 | 1 |

| Example-Cycle | 33-II (1 h) | 33-II (4 h) | 33-II (6.5 h) |
|---|---|---|---|
| % $BF_3$ | 39.8 | — | — |
| Temperature Peak | 45° C. | — | — |
| Product Lost to Cat. | 4.3% | — | — |
| Product Dist. | | | |
| $C_{10}$ | 8 | 11 | 8 |
| $C_{12}$ | 0 | 0.5 | 0.6 |
| $C_{20}$ | 74 | 54 | 29 |
| $C_{30}$ | 6 | 5 | 38 |
| $C_{40}$ | 12 | 29 | 24 |
| $C_{50}$ | 0 | 1 | 0 |

*In cycle II of Example 32 the entire catalyst layer from cycle I was used rather than the extracted layer, because of the difficulty of separating this catalyst from the hydrocarbon.
**Since the exotherm peak was below 50° C., the reaction mixture was externally heated to maintain the normal 50°-60° reaction temperature.
***In Example 32, no clear differentiation was made between $C_{10}$ and $C_{12}$ peaks and, accordingly, the $C_{12}$ material is included in the percentage for $C_{10}$.

After the two cycles indicated in Table X, the propylene glycol-$BF_3$ adduct was mixed with a $C_{10-12}$ distillate from earlier reactions of Example 26. This material did not polymerize indicating possibly a build-up of unreactive decene isomers. Thereafter the catalyst was isolated and used to catalyze polymerization of 1-decene in one cycle (IV) with the following results over time:

| Cycle | IV (1 h) | IV (4 h) | IV (6.5 h) |
|---|---|---|---|
| $C_{10}$ | 21% | 15% | 10% |
| $C_{12}$ | 0.4 | 0.6 | 0.7 |
| $C_{20}$ | 65 | 74 | 64 |
| $C_{30}$ | 9 | 4 | 15 |
| $C_{40}$ | 3 | 6 | 10 |
| $C_{50}$ | 2 | 0 | 0 |

Separability and Product Contamination

Table XI indicates qualitatively the separability of several alcohol-$BF_3$ adducts from the product hydrocarbon phase of decene polymerization. These values explain, in part, the "Prod. Lost to Cat.", "% $BF_3$ found in prod." and "% $BF_3$ lost in cat." values of the earlier tables.

TABLE XI

| Example | Alcohol (Complexed with $BF_3$) | Catalyst Layer | Separability |
|---|---|---|---|
| 22 | 1,4-Butanediol | Syrupy | Easy |
| 24 | 2,3-Butanediol | Syrupy | Easy |
| 25 | 1,3-Butanediol | Syrupy | Easy |
| 26 | Mannitol | Viscous | Very Easy |
| C31 | Butanol | Fluid | Difficult |
| C32 | Decanol | Fluid | Very Difficult |
| C33 | Propylene | Syrupy | Easy |

We claim:

1. In a method of reacting at least one unsaturated hydrocarbon in an alkyl transfer reaction of the type catalyzed by boron trifluoride, the improvement which comprises conducting the reaction in the presence of a catalytic amount of an adduct formed by saturating a butanediol with boron trifluoride and recovering the adduct from the reaction mixture and recycling the adduct.

2. The method of claim 1 wherein the polyhydric alcohol is 1,4-butanediol.

3. The method of claim 1 wherein the polyhydric alcohol is 2,3-butanediol.

4. The method of claim 1 wherein the polyhydric alcohol is 1,3-butanediol.

5. The method of claim 1 wherein said reaction is the alkylation with an olefinic hydrocarbon of 2-5 carbons of an aromatic hydrocarbon of 6-10 carbons.

6. The method of claim 5 wherein said olefinic hydrocarbon is propylene.

7. The method of claim 1 wherein said reaction is an oligomerization of an alpha-olefin of 4-20 carbons.

8. The method of claim 7 wherein said alphaolefin is 1-decene.

9. The method of claim 1 wherein the reaction is conducted at an elevated temperature at which the adduct is stirrable and the reaction mixture is cooled to a temperature at which the adduct becomes viscous before separation.

10. The method of claim 1 wherein the adduct contains at least about 0.3 mole of $BF_3$ per mole of hydroxyl of the polyhydric alcohol.

* * * * *